(12) United States Patent
Christian et al.

(10) Patent No.: US 7,440,098 B2
(45) Date of Patent: Oct. 21, 2008

(54) SPECTROSCOPE AND METHOD OF PERFORMING SPECTROSCOPY UTILIZING A MICRO MIRROR ARRAY

(75) Inventors: Sean M. Christian, Palm Harbor, FL (US); Jess V. Ford, Arnold, MO (US); Mike Ponstingl, St. Louis, MO (US); Sven Kruger, Berlin-Adlershof (DE); Margaret C. Waid, Medicine Park, OK (US); Bryan W. Kasperski, Azle, TX (US); Enrique Prati, Houston, TX (US)

(73) Assignee: Custom Sensors and Technology, Fenton, MO (US)

( * ) Notice: Subject to any disclaimer, the term of this patent is extended or adjusted under 35 U.S.C. 154(b) by 0 days.

(21) Appl. No.: 11/696,005

(22) Filed: Apr. 3, 2007

(65) Prior Publication Data

US 2007/0229821 A1 Oct. 4, 2007

Related U.S. Application Data

(60) Provisional application No. 60/744,246, filed on Apr. 4, 2006, provisional application No. 60/827,837, filed on Oct. 2, 2006.

(51) Int. Cl.
*G01J 3/08* (2006.01)
*G01J 3/18* (2006.01)
*G01J 3/42* (2006.01)

(52) U.S. Cl. .................. 356/319; 356/328; 356/330

(58) Field of Classification Search ............ 356/323, 356/325, 326, 328, 319, 310, 330
See application file for complete search history.

(56) References Cited

U.S. PATENT DOCUMENTS

| | | | |
|---|---|---|---|
| 5,128,797 A | 7/1992 | Sachse et al. | |
| 5,440,118 A | 8/1995 | Roscoe | |
| 5,504,575 A | 4/1996 | Stafford | |
| 5,629,125 A | 5/1997 | Leblans et al. | |
| 5,828,066 A | 10/1998 | Messerschmidt | |
| 6,128,078 A | 10/2000 | Fateley | |
| 6,504,943 B1 * | 1/2003 | Sweatt et al. ............... | 356/310 |
| 6,571,118 B1 | 5/2003 | Utzinger et al. | |
| 6,600,591 B2 | 7/2003 | Anderson et al. | |
| 6,678,050 B2 | 1/2004 | Pope et al. | |
| 6,753,960 B1 | 6/2004 | Polynkin et al. | |
| 6,768,105 B2 | 7/2004 | Mullins et al. | |
| 6,781,691 B2 | 8/2004 | MacKinnon et al. | |
| 7,265,830 B2 | 9/2007 | Wang | |
| 2004/0169858 A1 | 9/2004 | Da Silva | |
| 2004/0201850 A1 | 10/2004 | Hajian et al. | |

(Continued)

OTHER PUBLICATIONS

Schlumberger, "Fundamentals of Formation Testing," 2006, pp. 1-5, 27-29, 55-67, 99-124, 199-202, Schlumberger Marketing Communications, Sugar Land, Texas, United States.

Dudley, Dana, et al., "Emerging Digital Micromirror Device (DMD) Applications," DLP Products New Applications, Texas Instruments, Inc. undated.

(Continued)

*Primary Examiner*—F. L Evans
(74) *Attorney, Agent, or Firm*—Lewis, Rice & Fingersh, L.C.

(57) ABSTRACT

A spectroscope designed to utilize an adaptive optical element such as a micro mirror array (MMA) and two distinct light channels and detectors. The devices can provide for real-time and near real-time scaling and normalization of signals.

26 Claims, 10 Drawing Sheets

U.S. PATENT DOCUMENTS

| | | | |
|---|---|---|---|
| 2004/0239923 | A1 | 12/2004 | Adams et al. |
| 2004/0239931 | A1 | 12/2004 | Teichmann et al. |
| 2005/0185179 | A1 | 8/2005 | Wang |
| 2005/0243312 | A1 | 11/2005 | Geshwind et al. |
| 2007/0159625 | A1 | 7/2007 | DiFoggio |
| 2008/0174777 | A1 | 7/2008 | Carron |

OTHER PUBLICATIONS

Wagner, Eugene P. II, et al., "Construction and Evaluation of a Visible Spectrometer Using Digital Micromirror Spatial Light Modulation," Applied Spectroscopy, vol. 49, No. 11, 1995.

Ford, Joseph E., et al., "Dynamic Spectral Power Equalization Using Micro-Opto-Mechanics," IEEE Photonics Technology Letters, vol. 10, No. 10, Oct. 1998.

Duncan, Walter M., "Dynamic Optical Filtering in DWDM Systems Using the DMD," Solid State Electronics 46 (2002), pp. 1583-1585.

Lerner, J.M., et al., "The Optics of Spectroscopy—A Tutorial," Instruments SA, Inc., 1988.

Spudich, Thomas M., et al., "Potential for using a Digital Micromirror Device as a Signal Multiplexer in Visible Spectrscopy," Applied Spectroscopy, vol. 57, No. 7, 2003.

DeVerse, R. A., et al, "Realization of the Hadamard Multiplex Advantage Using a Programmable Optical Mask in a Dispersive Flat-Field Near-Infrared Spectrometer," Applied Spectroscopy, vol. 54, No. 12, 2000.

Badry, R., et al., "Downhole Optical Analysis of Formation Fluids," Oilfield Review, Jan. 1994.

Schroeder, R., "Slick Engineering," Spie's OE Magazine, May 2003.

Raghuraman, B., "Real-Time Downhold pH Measurement Using Optical Spectroscopy," SPE 93057, Society of Petroleum Engineers, 2005.

Sirkis, J., "Multifunctionality The Key in Challenging Instrumentation Markets," Lightwave Magazine, Mar. 2003.

Meyer, R., "RITMOS: A Micromirror-Based Multi-Object Spectrometer," Proceedings of the SPIE, 2004.

Smits, A.R., "In-Situ Optical Fluid Analysis as a Aid to Wireline Formation Sampling," SPE Formation Evaluation, Jun. 1995.

Texas Instruments, Application Report, "Single Panel DLP Projection System Optics," Mar. 2005.

Texas Instruments, Product Preview, "DMD 0.7 XGA 12° LVDS DMD Discovery," Jul. 2005.

Texas Instruments, Product Preview Data Sheet, "DMD 0.7 XGA 12° DDR DMD Discovery," Aug. 30, 2005.

Texas Instruments, "DMD Discovery 1100 Chip Set," 2004.

Texas Instruments, "DMD Discovery 3000 Digital Controller (DDC3000) Starter Kit Technical Reference Manual," Oct. 2005.

Texas Instruments, "DMD Discovery 1100 Controller Board and Starter Kit," Oct. 2004.

Texas Instruments, "DMD Discovery 1100 Controller Board GUI User's & Programmer's Guide," Sep. 2004.

Baker Hughes, "RCI Reservoir Characterization Instrument," 2000.

Baker Hughes, "SampleView" 2000.

International Search Report, International Patent Application No. PCT/US2007/080112, mailed on Mar. 25, 2008.

* cited by examiner

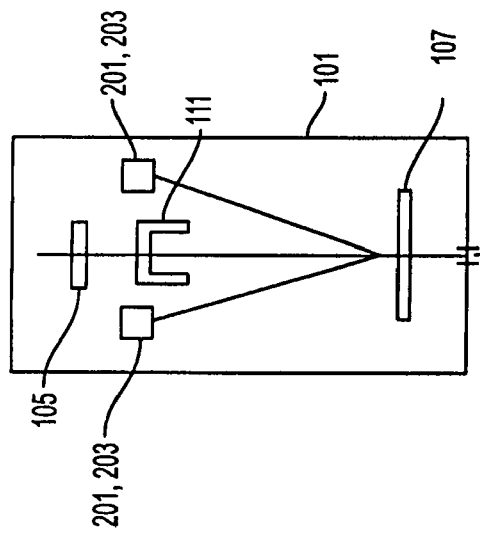
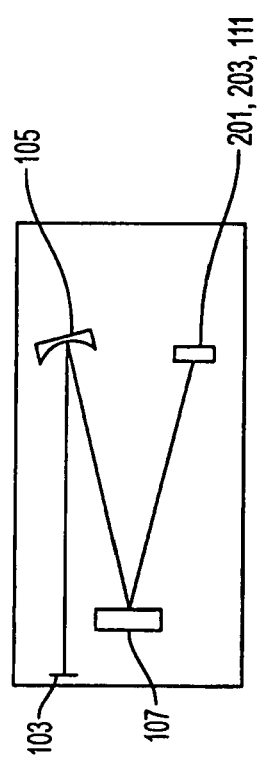
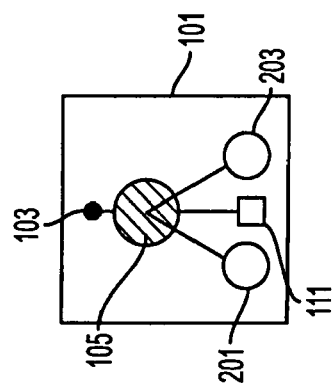
FIG. 3A
FIG. 3B
FIG. 3C

SPECTROSCOPE AND METHOD OF PERFORMING SPECTROSCOPY UTILIZING A MICRO MIRROR ARRAY

CROSS REFERENCE TO RELATED APPLICATIONS

This application claims benefit of U.S. Provisional Patent Application Ser. No. 60/744,246, filed Apr. 4, 2006, and U.S. Provisional Patent Application Ser. No. 60/827,837, filed Oct. 2, 2006. The entire disclosure of both documents is herein incorporated by reference.

BACKGROUND

1. Field of the Invention

This invention relates generally to the field of spectroscopy and spectrum analysis, more particularly, to a device for optical or other spectral measurement that utilizes a Micro Mirror Array (MMA) to provide real-time scaling or normalization by providing a sample and reference channel.

2. Description of the Related Art

Spectroscopes such as spectrophotometers, spectrometers, spectrofluorometers, or spectrum analyzers are used in numerous situations to detect and provide the spectral characteristics of a test sample. These characteristics can then be used to provide an analysis of the composition of the sample for scientific or industrial analysis. Because of the ability of a spectroscope to provide information on a broad range of samples and sources, they have seen use in a wide number of industries and activities ranging from police forensics, to scientific analysis, to industrial monitoring.

Because spectroscopes utilize some form of electromagnetic radiation (the spectrum which they utilize) to perform their analysis, they necessarily are dependent on a number of factors in their design. Originally, spectroscopes were large devices due to the necessity of splitting the electromagnetic radiation into its components and often those devices were limited in the ability to perform real-time spectral analysis or partial spectral analysis.

Further, systems which utilize spectrum analysis were constrained by their ability to utilize only a limited number of spectral analysis techniques by their hardware configuration. Once built, generally the spectrum can only be analyzed temporally or spatial, not both. Further, spectroscopes are also dependent on their ability to remain calibrated as they analyze or scan. Spectroscopes generally require constant operator interaction to adjust for differing situations and to continually check and/or re-establish calibration.

SUMMARY

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other problems in the art, described herein is a spectroscope which utilizes an adaptive optical element such as a Micro Mirror Array (MMA) and which is capable of providing real time scaling or normalization by utilizing two separate collection channels or light paths.

Described herein, among other things, is a spectroscope comprising: a Micro Mirror Array (MMA) comprising a plurality of mirrors; each of the mirrors being switchable between a first and a second position; a light source having a spectrum; and at least two detectors; wherein the light source is spatially dispersed across the MMA in such fashion that a first group of the mirrors, can direct a first portion of the spectrum along a first light path to a first of the at least two detectors by being placed in the first position; and wherein a second position of the mirrors can direct a second portion of the spectrum along a second light path to a second of the at least two detectors by being placed in the second position.

Depending on embodiment of the spectroscope the light source may be a broad band light source or a narrow band light source. The first light path includes a sample to be analyzed while the second light path does not include a sample to be analyzed so the output from the second detector can be used as a reference for output from the first detector.

In an embodiment, the MMA comprises a Digital Micromirror Device (DMD).

In another embodiment, the spectroscope further comprises an input slit through which the light passes prior to reaching the MMA. Columns of the spectrum can correspond to a spectral dimension of dispersion and rows correspond to a spatial dimension of the input slit. The plurality of mirrors may be arranged into a plurality of rows and columns wherein the columns of the spectrum are incident on the MMA so as to align with the columns of mirrors or wherein the columns of the spectrum are incident on the MMA so as to align with a diagonal of the rows and the columns of the mirrors In another embodiment, the MMA performs spectral separation of the spectrum.

In another embodiment, the MMA can reversibly direct the first portion along the first and the second path and the second portion along the first and the second path in such fashion that when one of the portions is directed to the first path, the other of the portions is directed to the second path and vice-versa.

There is also described herein a method of performing spectroscopy, the method comprising: providing a spectroscope including: a Micro Mirror Array (MMA) comprising a plurality of mirrors; each of the mirrors being switchable between a first and a second position; and at least two detectors; separating light into a spectrum; directing the spectrum to the MMA such that a first portion of the spectrum is incident on a first group of the mirrors and a second portion of the spectrum is incident on a second group of the mirrors; instructing the MMA to arrange the first and the second group of mirrors such that: the first portion is directed down a first light path including a sample to be analyzed to a first of the detectors; and the second portion is directed down a second light path which does not include the sample to be analyzed to a second of the detectors; instructing the MMA to arrange the first and the second group of mirrors such that: the second portion is directed down the first light path to a first of the detectors; and the first portion is directed down the second light path to a second of the detectors; comparing an output from the first and the second detector to provide an indication of the composition of the sample.

In an embodiment of the method, in the step of comparing, the spectrum has been temporally structured by the steps of instructing. The temporal structuring may be dependent on wavelength in the spectrum such as to enable simultaneous processing of each of the wavelengths.

In another embodiment of the method, in the step of comparing, the spectrum has been spatially structured at least in part by the steps of instructing. The spatial structuring may also be dependent of wavelength in the spectrum.

In embodiments of the method, in the step of comparing the spectrum may have been temporally encoded so as to optically chop the spectrum to improve a signal-to-noise ratio by the steps of instructing, the spectrum may have been dynamically scaled at least in part by the steps of instructing, the spectrum may have been dynamically filtered at least in part by the steps of instructing, or the spectrum may have had the resolution dynamically altered at least in part by the steps of instructing.

In another embodiment of the method in the step of comparing a signal-to-noise ratio has been dynamically increased at least in part by the steps of instructing.

In an embodiment of the method, the second light path does not include any samples prior to the second detector or may include a reference sample such as, but not limited to, a gas correlation cell.

There is also described herein, a spectroscope comprising: an adaptive optical element capable of directing a first wavelength band along a first light path and a second wavelength band along a second light path when both the bands are simultaneously incident on the adaptive optical element; a light source having a spectrum; and at least two detectors; wherein the light source is spatially dispersed across the adaptive optical element in such fashion that a first wavelength band in the spectrum is directed along the first light path to a first of at least two detectors; and wherein a second wavelength band in the spectrum is directed along the second light path to a second of at least two detectors.

BRIEF DESCRIPTION OF THE DRAWINGS

FIG. 2 is a conceptual diagram of the dual channel processing capabilities of an embodiment of a spectroscope.

FIG. 3 provides a side (FIG. 3A), top (FIG. 3B), and end (FIG. 3C) view of the internal design of a first embodiment of a spectroscope.

FIG. 11 provides a graph of how the spectroscope can be used for dynamic filtering. FIG. 11A shows a graph before filtering while

DESCRIPTION OF THE PREFERRED EMBODIMENT(S)

Figure 1:
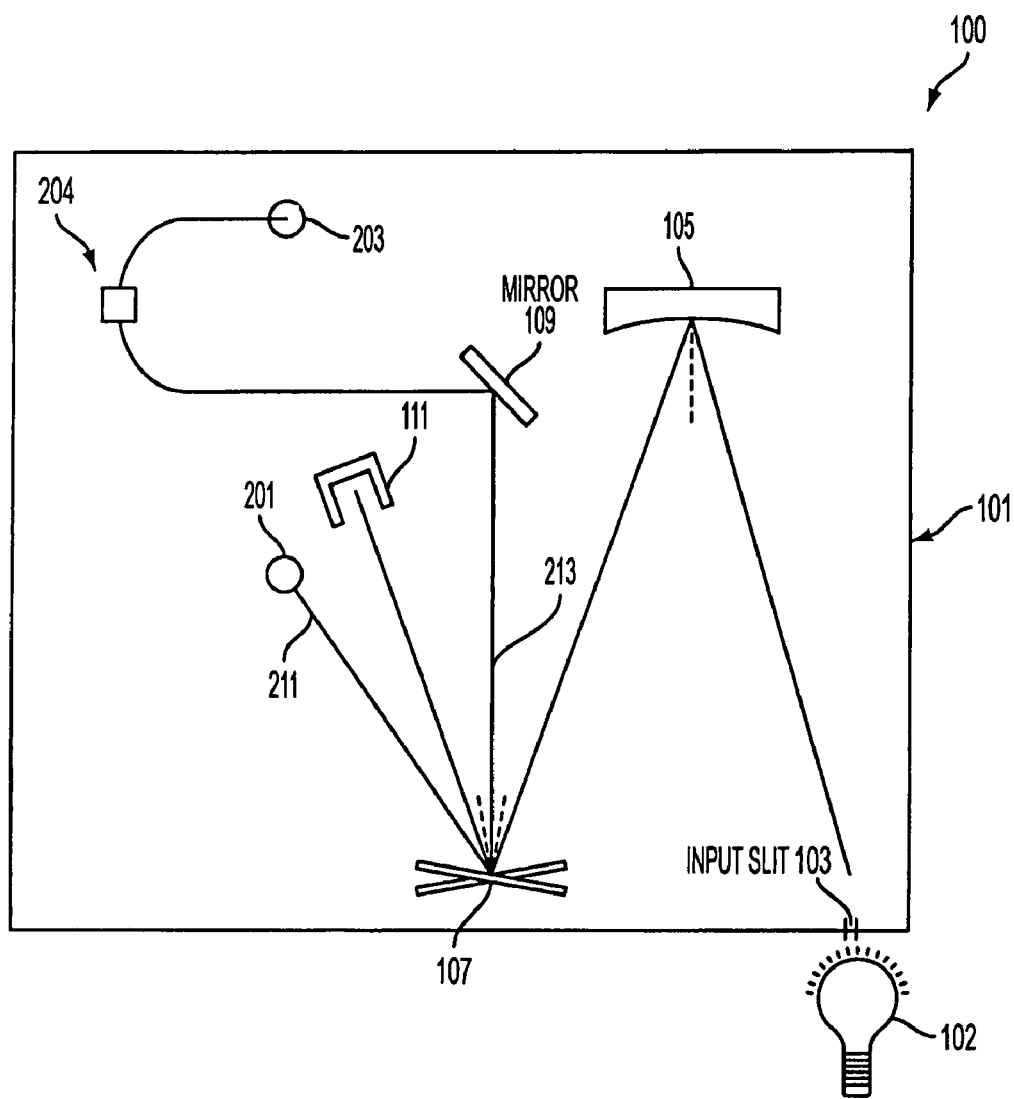
FIG. 1 is a conceptual diagram of an embodiment of a spectroscope utilizing multiple channels.

Generally a spectroscope (100) as described herein is used for optical spectral measurement. Electromagnetic radiation is delivered to the spectroscope (100) as is understood by one of ordinary skill in the art, such as, but not limited to, via optical fiber or free-space delivery from a predefined source (102). Throughout this disclosure, this document will refer to the incident electromagnetic radiation as "light" and the source (102) as a "light source", but this is in no way intended to limit the radiation which may be used to any particular radiation.

Further, while the embodiments of the spectroscope (100) discussed herein are capable of manipulating all wavelengths of electromagnetic radiation, the remaining discussion will focus on the wavelength ranges of the ultraviolet, visible, near infrared and mid infrared regions as the electromagnetic spectrum being used. Further, the radiation will be referred to using the term "light" even though the spectrum is intended to include wavelengths outside the bounds of visible light.

The light source (102) will generally comprise a broadband light source emitting a number of different wavelengths of light simultaneously such as, but not limited to, natural solar radiation, a tungsten filament, or any combination of narrow band sources. In an alternative embodiment, the light source (102) may comprise a single narrow band or single wavelength source such as, but not limited to, light emitting diodes or lasers; an electrically charged gas such as neon that emits a narrow band or a number of narrow bands, or any other light source known to those of ordinary skill in the art. The light can be provided to the spectroscope (100) device discussed herein by any method known to one of ordinary skill in the art including, but not being limited to, being reflected, refracted, focused, or diffused prior to reaching the spectroscope (100).

While this disclosure will also generally refer to the devices discussed herein as "spectroscopes" it should be recognized that this term is not being used to refer to a particular type of spectral evaluation device but is intended to refer generally to a class of devices used in conjunction with the review, evaluation, or analysis of spectrums. It is not required that all spectrum evaluations or analysis devices used in a spectroscope be used in this device. The device can be used in any kind of real-time or other process spectroscopy monitoring including, but not limited to, optical monitoring, spectrophotometry, spectrofluorometry, spectrum analysis, spectrocolorimetry, and spectroradiometry. Additionally, the device can be used in laboratory based analyses or other processes similar to those described above.

Generally, the spectroscope (100) includes optical components to shape, manipulate, or route incident light to targets of interest, spectrally disperse incoming light, image the dispersed light onto a spatial, spectral, or temporal filtering device, direct the filtered light onto, into, or around (bypassing) a sample, and then direct the light to some type of optical detector. The spectroscope (100) of the present disclosure provides for multiple detectors each of which is associated with its own optical channel, or light path. In the depicted embodiments, two channels are shown as this is generally the preferred number, however, in alternative embodiments more may be used.

In FIG. 1 the two detectors (201) and (203) are accessed through one of two optical channels (211) and (213). One optical channel (213) is capable of directing light to a sampling accessory (204), such as, but not limited to, a fiber optic probe, a cuvette assembly, or another device as would be understood by one of ordinary skill in the art. The second optical channel (211) is generally used as an optical reference channel for calibrating and therefore does not include a sampling accessory (204). However, in an alternative embodiment the second optical channel (211) could be used as a secondary data channel in some applications, such as spectroradiometery or spectralfluorimetry, to improve Signal-to-Noise (S/N) and/or to enhance data sampling rates in which case a sample could be provided. In this embodiment, one light path is therefore used to interrogate the sample, while the other is directed to bypass (not interrogate) the sample.

Throughout this disclosure these channels (211) and (213) or light paths may be referred to as a "sampling channel" and a "reference channel." This is to refer to the fact that the sample channel (213) is generally used when the electromagnetic radiation is directed through a sample while in the reference channel (211) the light is generally not directed through that sample, but is used for reference. One of ordinary skill in the art, however, would recognize that the channels could be reversed in roles depending on embodiment and none or both of the channels could include sample depending on the desired operation. For example, the reference channel (211) could include a gas correlation cell in an embodiment.

FIG. 1 provides a block diagram showing the conceptual layout of an embodiment of a spectroscope (100) of the present invention. The device of FIG. 1 generally comprises a housing (101) into which other components are placed to shield them from ambient light. The housing (101) includes an input aperture (103) such as a slit which will serve to provide the incident light to be used in the spectroscope. The use of a slit will result in the light generally having a spread spectrum of height depending on the height of the slit. The light source (102) may alternatively be provided in the housing (101) in which case it would have a predefined path formed in the housing (101) for forming a light input of desired shape and size. The incident light source (102) will generally provide light of a number of different wavelengths (broadband light). The incident light that passes through the slit (103) is directed onto a grating (105), prism, or other surface capable of separating the light into its spectrum, which is used to spatially disperse light as a function of wavelength.

This light is then projected onto an adaptive optical element which is some form of device which can change its surface or other optical property to change the direction that light incident on it is directed. In an embodiment, this comprises an array of individually moveable mirrors. In the preferred embodiment, this is a microoptomechanical (MOM) device comprising a Micro Mirror Array (MMA) (107). In an embodiment, the MMA (107) comprises a Digital Micromirror Device (DMD) such as those manufactured by Texas Instruments. The MMA (107) will generally comprise a large number of mirrors of very small size which are arranged in a recognized pattern. In most embodiments, this will be a grid. The mirrors on the MMA (107) are generally independently positionable via a control system, (not shown) to at least two different positions. The MMA mirrors also can move between at least those two positions when such movement is requested by the control system. In the depicted embodiment where the MMA is a DMD, the two positions are generally +10° and −10° from a predetermined horizontal position (0° position).

Figure 4:
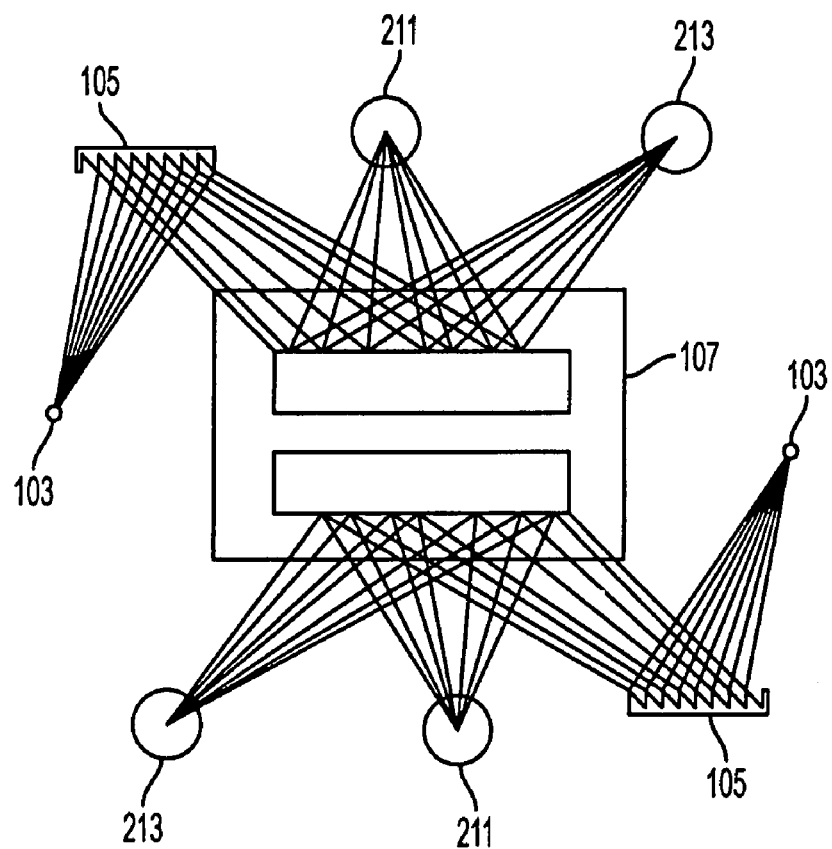
FIG. 4 provides a conceptual diagram of the internal design of a spectroscope using two separate inputs and measuring two samples.

FIG. 3 provides a series of general block diagrams of embodiments of the spectroscope shown in the conceptual diagram of FIG. 1. Not shown for clarity are the optical elements (205) used to image the spectrally processed light (i.e. post MMA (107)) into the individual channels. These figures are provided to show a possibility for how an actual optical path using the MMA (107) and two sample channels can be accomplished. FIG. 4 provides for a conceptual layout of a spectroscope which includes two light inputs and essentially provides for four light paths by providing two spectroscopes (100) in the same housing (101) and using the same MMA (107).

Figure 6:
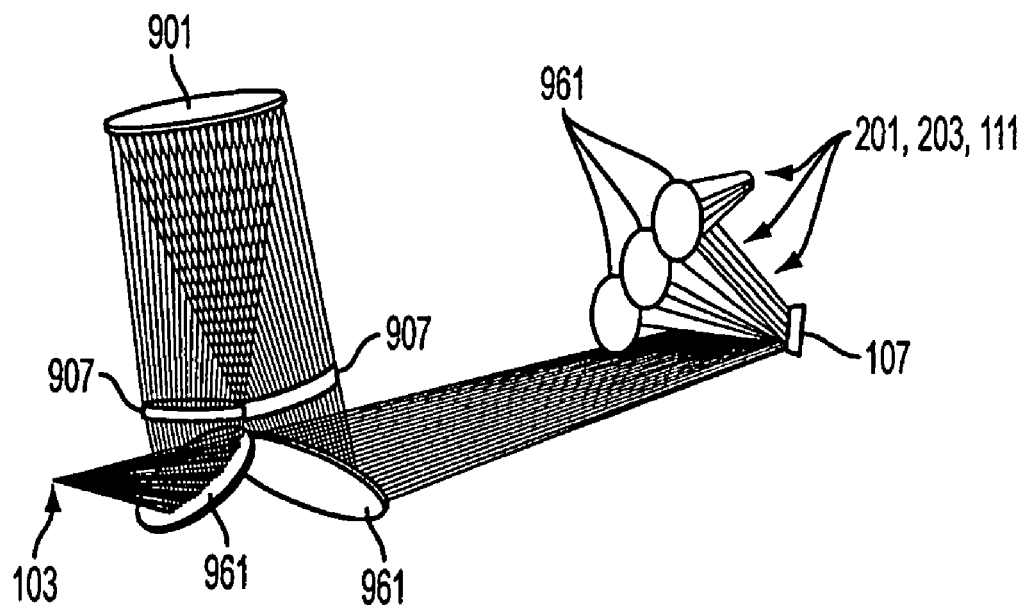
FIG. 6 provides for an embodiment of an optical path.
Figure 7:
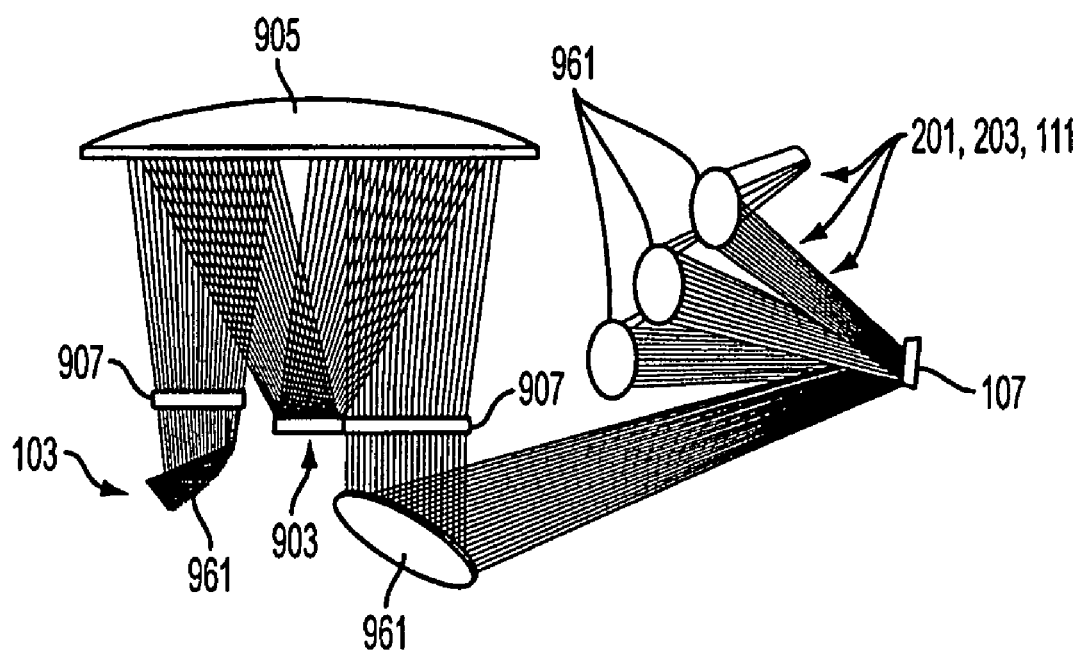
FIG. 7 provides for an alternative embodiment of an optical path.
Figure 8:
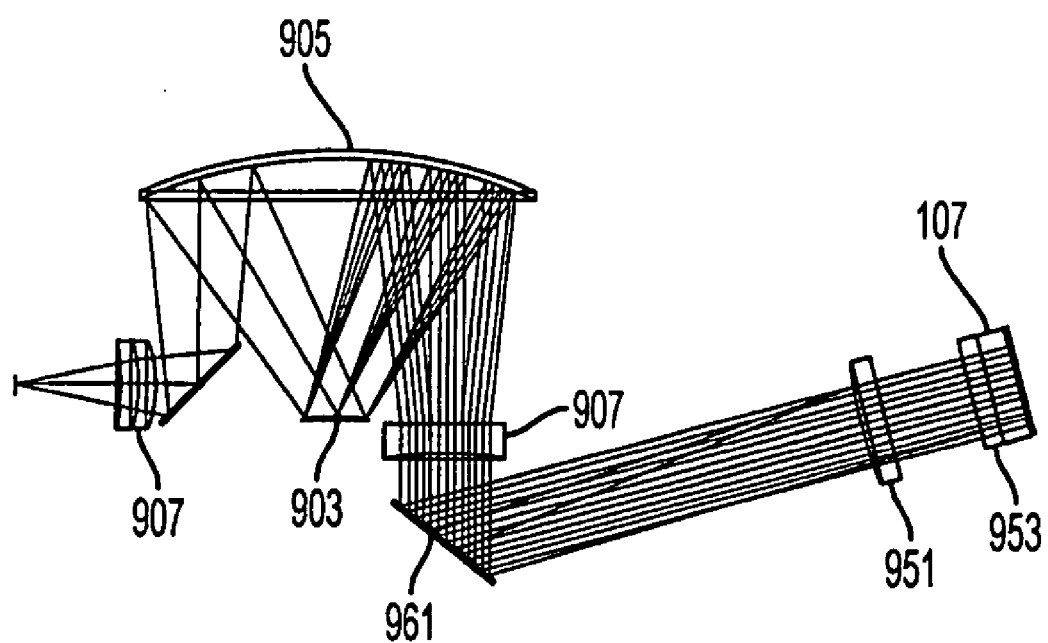
FIG. 8 provides for another embodiment of an optical path.

Light incident on the MMA (107) will be routed from the slit (103) and grating (105) and potentially, may be further manipulated to improve, among other things, its shape, dispersion, or intensity. FIGS. 6 through 8 provide for a number of embodiments of a spectroscope showing light path manipulation prior to the MMA (107). The various embodiments can include concave diffraction gratings (901), convex diffraction gratings (903), concave mirrors (905) or lenses (907) to manipulate the light spectrum prior to it being incident on the MMA (107). In the embodiments of FIGS. 6 through 8 there are also included a number of other light handling objects prior to the MMA including relay mirrors (961), lenses (907), and a telecentric lens (951) which is added to make all light incident on the MMA (107) normal (perpendicular) to the MMA (107) face. There may also be included a filter (953). In this configuration, the spectrometer (100) can be used to recombine the light into the reference channel (211) or sample channel (213). The design of FIG. 8 can provide for an athermal spectrometer (100) which can provide for improved resolution and accuracy of resultant readings over a large number of temperature readings.

The light incident on the MMA (107) is generally in the form of a spread spectrum. That is, the component wavelengths of the light will be spatially separated from each other by being bent through different angles at a time prior to being incident on the MMA (107). Such light will generally have a spectrum going from light having longer wavelength (red and infrared) to light being shorter wavelength (violet and ultraviolet). The spectrum of light (801) is shown as the dark outline rectangle (801) in FIG. 5 with the one end representing shorter wavelength light and the other end longer wavelength light. It should be recognized that points directly vertical of each other in FIG. 5 are the same wavelength. Therefore making "rows" in the spectrum correspond to the spatial dimension of the input slit, while "columns" in the spectrum correspond to the spectral dimension of dispersion.

The MMA (107) is positioned in the housing (101) so that some or all of the various wavelengths incident on the MMA (107) are directed into the two different channels (211) and (213), each of which are associated with a detector (201) or (203) based on the positioning of the various mirrors of the MMA (107). Light routing is dependent on the specific MMA (107) mirror position relative to the incident radiation. That is, the wavelengths are "spectrally" filtered by the MMA (107) between the light channels (211) and (213). In order to direct specific wavelengths of the incident light within the appropriate channel (211) or (213), devices such as mirrors (961) can be placed in the various paths to direct the wavelengths incident on them as appropriate for that channel (211) or (213).

It is important to recognize that the MMA (107) does not act as a beam splitter or other device which sends part of the intensity down each path. Instead, the MMA (107) sends a portion of the spectrum down each path exclusive of the other. For example, the MMA (107) could send the red, orange, yellow, and green portion of the visible spectrum down one path and the blue, indigo, and violet portion of the same spectrum down the other path. This would mean that if the first path is reference channel (213), detector (203) would not have any blue, indigo or violet incident thereon at that time.

Alternatively or additionally, a series of order sorting filters, folding mirrors, and/or collimating lenses or focusing lenses (205), can be utilized to collect and image polychromatic, or, monochromatic, light from the MMA (107), onto the appropriate detectors (201) or (203) for spectral processing. One should recognize that the embodiment of FIG. 8 allows for mirrors and other components to be used for a number of different purposes depending on whether light is incident on, or reflected from the MMA (107). In another embodiment, the spectrum incident on the MMA (107) can be temporally structured or spatially filtered in addition to or instead of the spectral filtering discussed.

Detectors (201) and (203) may measure any form or spectrum of light and, in an embodiment, detectors (201) and (203) utilize two single element photodiodes (PDs) as detectors. In an alternative configuration the detectors (201) and (203) could utilize two dimensional (2D) charge coupled devices (CCDs) or photo diode arrays (PDAs). In still further embodiments, the detectors (201) and (203) comprise, but are not limited to Photo Multiplier Tubes (PMTs), Avalanche Photo Diodes (APDs), CMOS detectors, Bolometers, any other detector known to those of ordinary skill in the art, or any combination of these detectors.

In the embodiment of FIG. 1, the spectroscope (101) is preferably attached to a sampling accessory (204) which allows one channel of light to interact with a test sample and then to return the output radiation to the sample detector (203) and eventually the control system. The sampling accessory (204) could be, but is not limited to, a fiber optic based accessory, a transmission dip probe, a reflectance probe, a fluorescence probe, an extractive flow cell, other sampling devices known to those of ordinary skill in the art, or any combination of sampling devices.

Figure 2A:
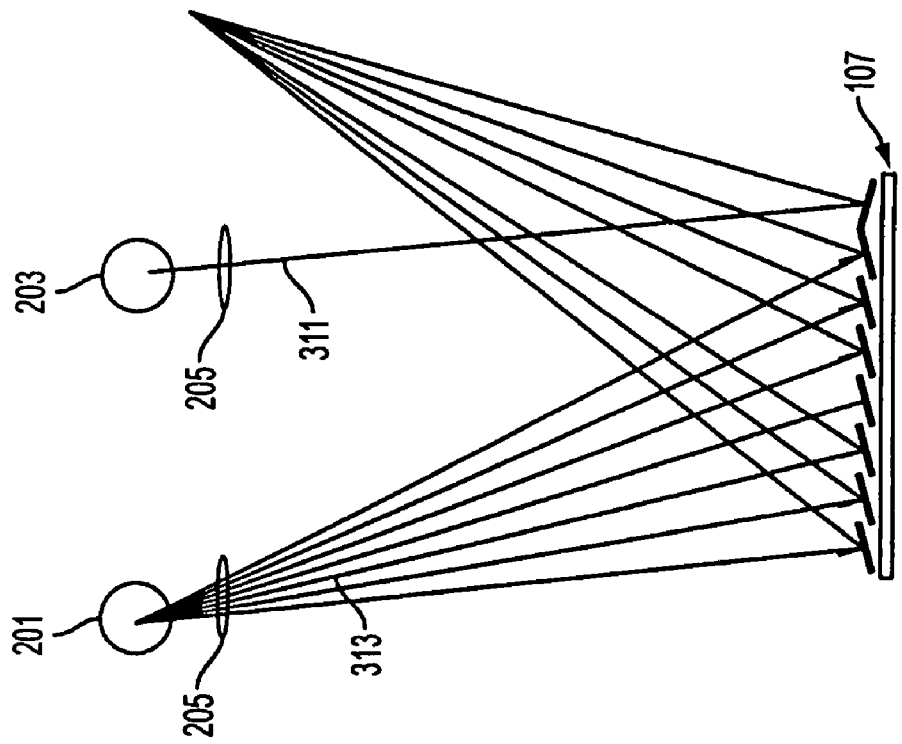
FIG. 2A shows a first wavelength directed to the reference channel with all other wavelengths directed to the sample channel.

FIG. 2 illustrates a conceptual drawing of a potential sampling mode of the spectroscope (100) of FIG. 1. In FIG. 2, the MMA (107) is used as a spectral filter, with sampling occurring using one or more narrow bands of radiation at a time. FIG. 2A illustrates spectral filtering where a single narrow band of radiation (or even single wavelength) is used to probe the sample. The selected band is narrow band (311). In FIG. 2A, this band (311) would be traveling down the reference channel (211) and is therefore incident on the reference detector (201) while the remaining bands (313) are traveling down sample channel (213) and are imaged on the sample detector (203). Therefore, in this situation, the band (311) is not incident on the sample but is bypassing the sample. Since this band (311) is desired for sample interrogation, the signal generated by the band (311) at the reference detector (201) in this situation therefore represents a "non-sample" signal which can be used as a reference. The output of the sample detector (203) in this arrangement is being generated from a portion of the spectrum which may or may not be of interest, but the output from which is often ignored. In particular, the intensity, dispersion, wavelengths, bandwidth, or any other characteristic of the band (311) may be detected by detector (201). That is, a base or reference determination of the band (311) may be established.

Figure 2B:
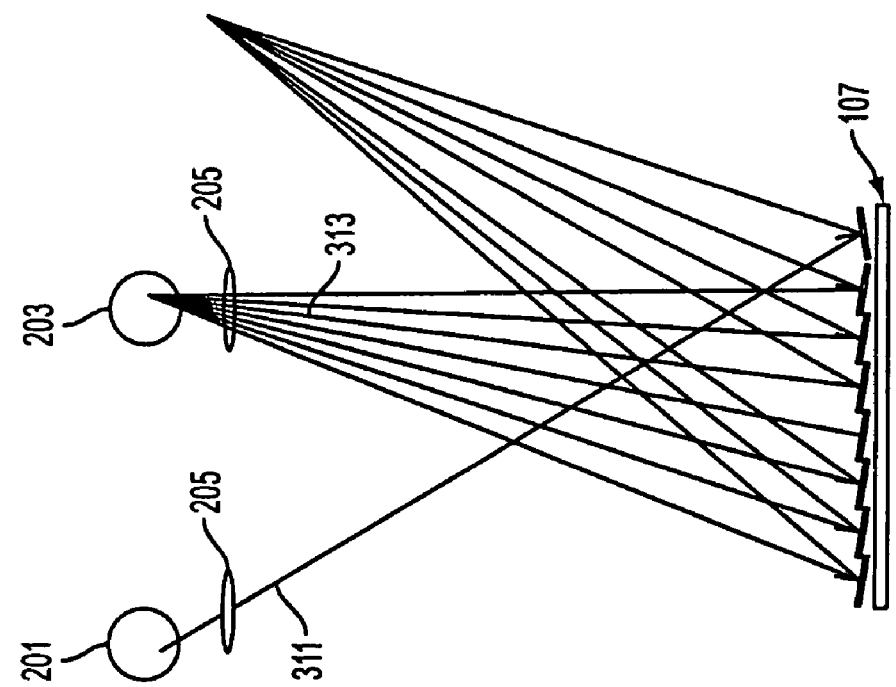
FIG. 2B shows the first wavelength directed to the sample channel with all other wavelengths directed to the reference channel.

In FIG. 2B the band (311) is now directed down the sample channel (213) to the sample detector (203) with the remaining bands (313) directed down the reference channel (211) to reference detector (201). Now the output of sample detector (203) is of interest as the sample is being interrogated by the desired spectrum. The percent transmission or absorbance or other measurable values can be calculated based on measurements from both the sample and reference channels by comparing the output of the detectors (201) and (203). As should be apparent, because the switch between the two channels having the spectrum of interest can occur relatively quickly and repeatedly, the output of the reference detector (201) can be used to normalize the output of the sample detector (203) to provide for a scaled reading. So as to provide for the most accurate referencing, the two detectors (201) and (203) will generally be similar so that the output of the light interacting with the sample and not interacting with the sample are incident on similar detectors.

As should be apparent from FIG. 2, the switching of the band (311) from reference detector (201) to sample detector (203) (and the corresponding movement of bands (313)) is accomplished by adjustment of the state of the individual mirrors in the MMA (107). In particular, referring to FIG. 5, the spectrum incident on the MMA (107) is spread across the mirrors of the MMA (107) so that different wavelengths are incident on different portions of the MMA (107) generally with an individual wavelength, or small wavelength band being incident on each mirror in the array as shown. Each individual mirror component of the MMA (107) can be adjusted independently between at least the two different states as previously discussed. This allows for each of the bands (311) and (313) in FIG. 2 to be independently sent to either the reference (201) or sample (203) detector simply by a selected arrangement of the mirrors.

In the embodiment of FIGS. 1 and 2 the mirrors will generally be independently arranged at two different states having different angular positions. Generally, these two different positions may be angularly symmetrical about a midpoint location simply for position stability. For example, if the midpoint was classified as a 0° state, the two positions can be a +X and −X degree state from the 0 position. The midpoint is also preferably chosen to correspond to the position where the individual mirror on the MMA is arranged generally parallel to the substrate of the MMA.

Figure 5A:
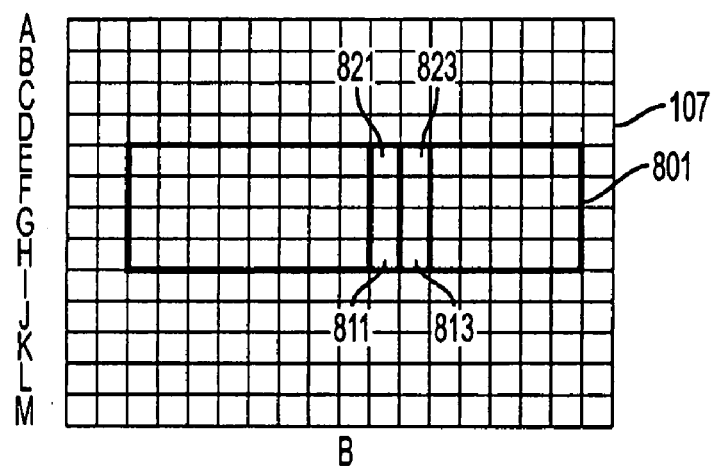
In FIG. 5A, the spectrum is aligned with the MMA, while in FIG. 5B the spectrum is angled across an MMA.

The incident light is preferably directed toward the MMA (107) in such a way that the change in each mirror, or more particularly changes in a row, column or diagonal of mirrors can direct a particular wavelength or narrow band of wavelengths to a particular path. Two different methodologies for this are shown in FIG. 5. In FIG. 5A, the spectrum (801) is incident on the MMA (107) grid so as to generally align each frequency of light with a column (or row) of mirrors. For reference, column (811) in this case is generally aligned with a small band of wavelengths (821) in the middle area, while column (813) is generally aligned with a small band of wavelengths (823) neighboring band (821). Other bands would be aligned with other columns in a similar fashion. Should the band of wavelengths (821) in column (811) be desired for measuring, the mirrors in that column (811) will be offset from the other mirrors on the MMA (107) in their position. Specifically, the column (811) will generally be at position +X (corresponding, for example, to light channel (211)) when the remaining columns (including column (813)) are generally at position −X (corresponding, for example, to light channel (213)) and vice-versa.

As is readily apparent, a single column need not be segregated and any single column or combination of columns, up to and including all columns can be included in the segregation. Each of the segregated columns may then be used to interrogate the sample and be referenced as the MMA (107) mirrors shift between positions. As should also be recognized, the unselected columns can also additionally or alternatively be used to interrogate the sample as the two groups cycle between the two channels (211) and (213).

Figure 5B:
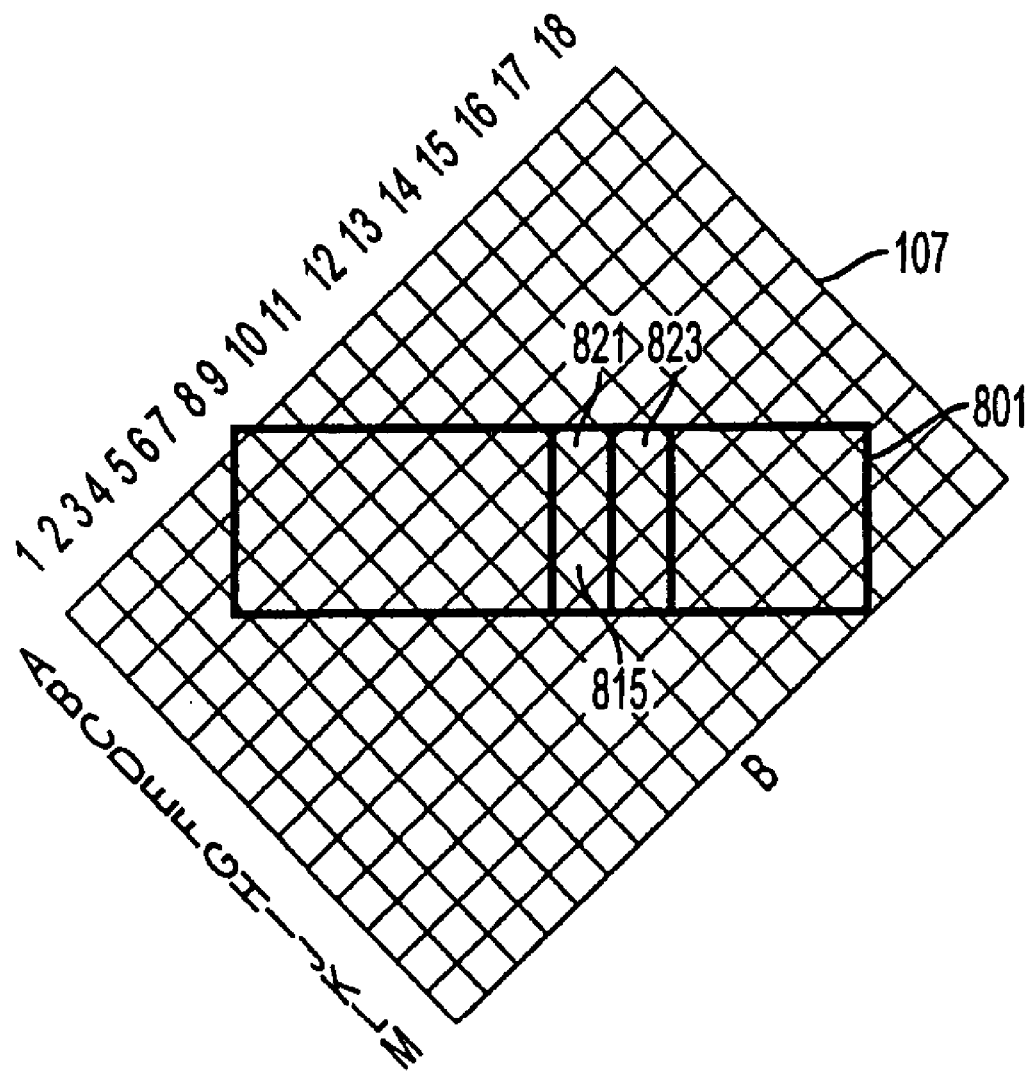
FIG. 5 provides for positioning of a spectrum on an MMA.

FIG. 5B provides for an alternative arrangement. In FIG. 5B the spectrum band (821) is arranged on a diagonal (815) with the MMA (107). This provides much of same functionality of FIG. 5A, but because of the orientation of each mirror relative the spectrum (with part of each band overlapping neighboring bands) an additional form of optical smoothing can be achieved by segregating various diagonals instead of columns.

The ability of the MMA (107) to provide for any number of wavelength bands, as selected, being used for the evaluation can allow the spectroscope (100) to perform a large number of dynamic adjustments on the resultant signals received from the sample. Because the wavelength bands (821) can be individual segregated and therefore acted upon, a user can select the nature of their interrogation of the sample in a wavelength dependent fashion.

Figure 9:
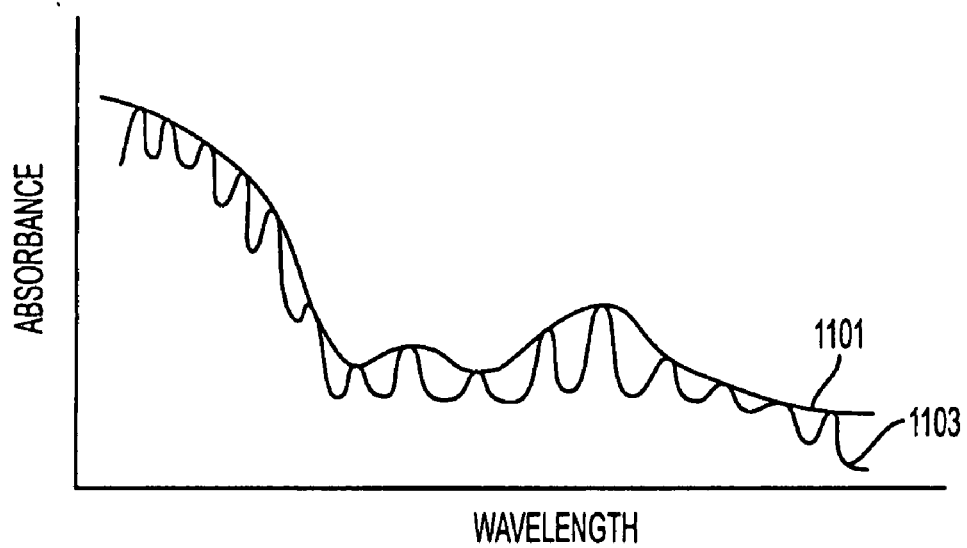
FIG. 9 provides for a graph showing how the spectroscope can be used for dynamic resolution control.

For example, FIG. 9 provides for a hypothetical graph showing the MMA (107) being used to allow for dynamic resolution control. The line (1101) is a much smoother curve and can be generated by having a large number of columns (811) be selected to interrogate simultaneously. On the other hand, line (1103) can be generated by having each individual column be used to interrogate separately. In this latter situation, the determination is much more exact as to absorbance of a smaller wavelength band, but the evaluation will generally take more time. Depending on the type of data output desired, one can select the mode of operation at the time of use.

Figure 10:
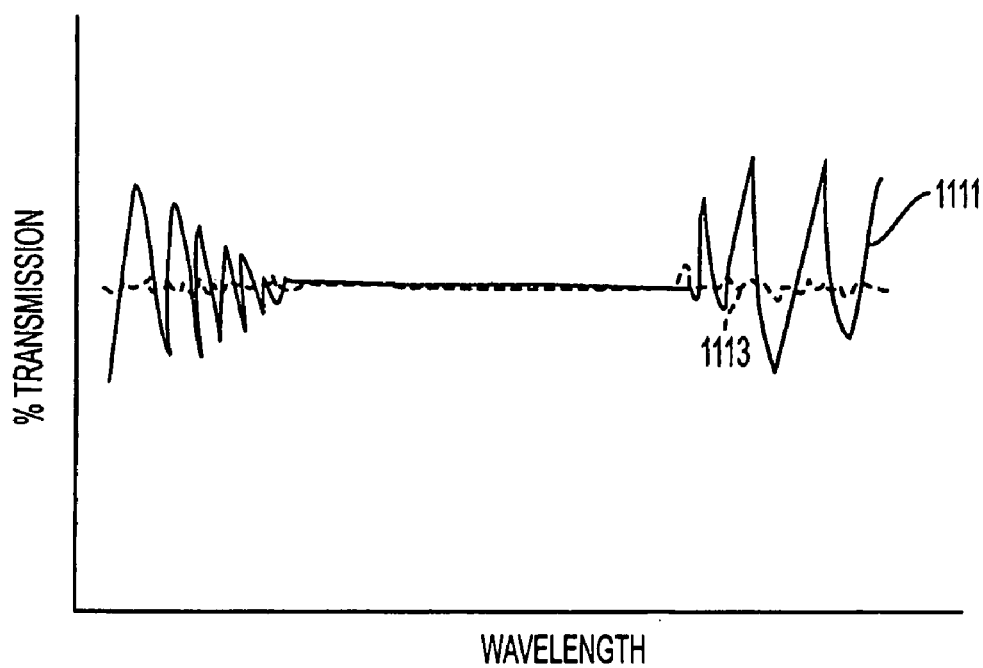
FIG. 10 provides a graph of how the spectroscope can be used to improve dynamic signal to noise ratio.

FIG. 10 provides for another such wavelength dependent structuring of the interrogation. In this hypothetical, the MMA (107) is used to dynamically improve signal to noise. Line (1111) is a noisy signal at both ends representing the normal occurrence with broad band light sources. The dashed line (1113), provides that the MMA can provide less light intensity in the center areas by cycling these wavelengths to shine on the detector less. This allows the detector to integrate over a longer period of time which allows the end wavelengths to shine on the detector for an equivalent period of time as the center areas effectively leveling out the percentage of transmission at all wavelengths. Alternatively, one skilled in the art would recognize that signal-to-noise can be equilibrated by controlling the mirrors' duty cycle, or by simply scaling the integration time for each band (821) so that the equivalent signal response results from each band being measured. In doing so, the reference channel could also be measured in a comparable fashion.

Figure 11A:
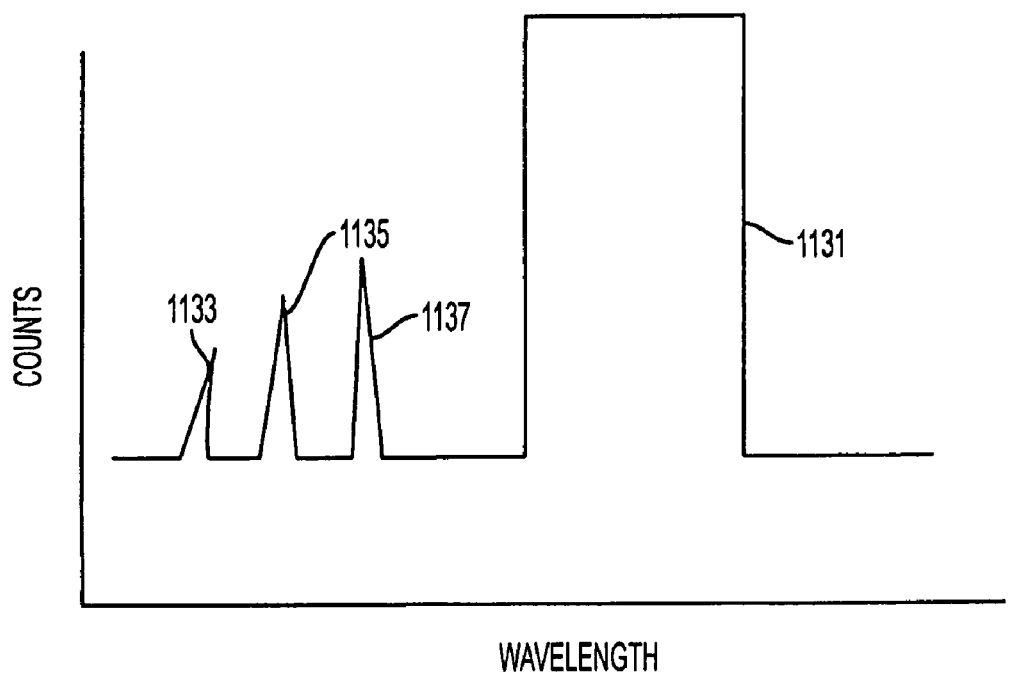
Figure 11B:
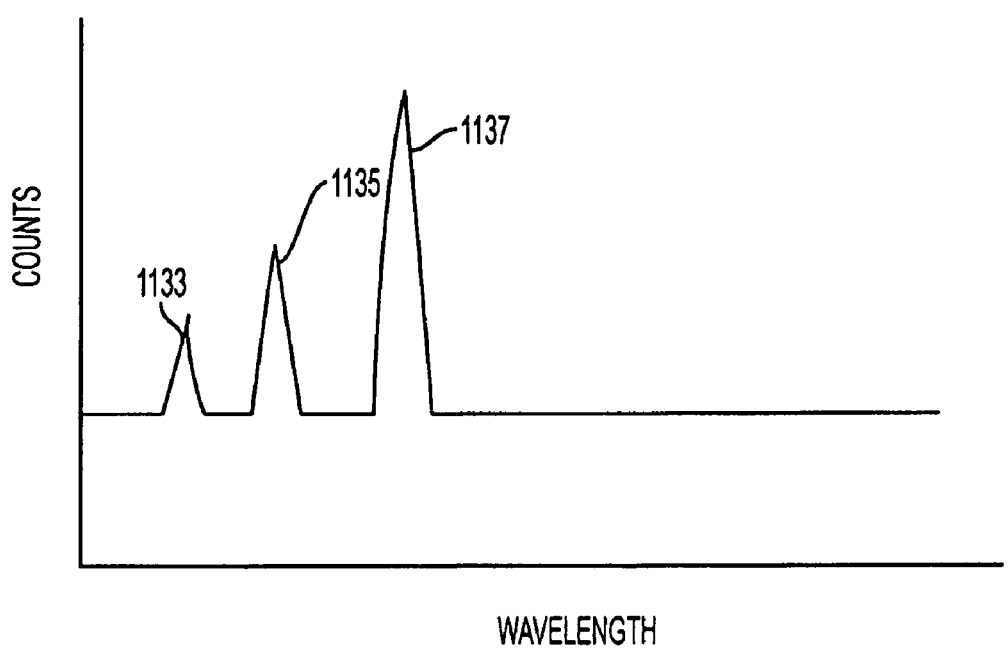
FIG. 11B shows the same graph after filtering.

FIG. 11 provides a representation of dynamic filtering. In FIG. 11A, there is provided a particular wavelength band (1131) of light which represents a saturated signal response. In many applications, such a saturated signal response may obscure or bias the details of the smaller signal responses (1133), (1135), and (1137). In FIG. 11B, the sections of the spectrum corresponding to the problematic wavelengths have been cut out, eliminating any transmission at that wavelength and allowing the smaller peaks (1133), (1135), and (1137) to be relatively more prominent.

Figure 12:
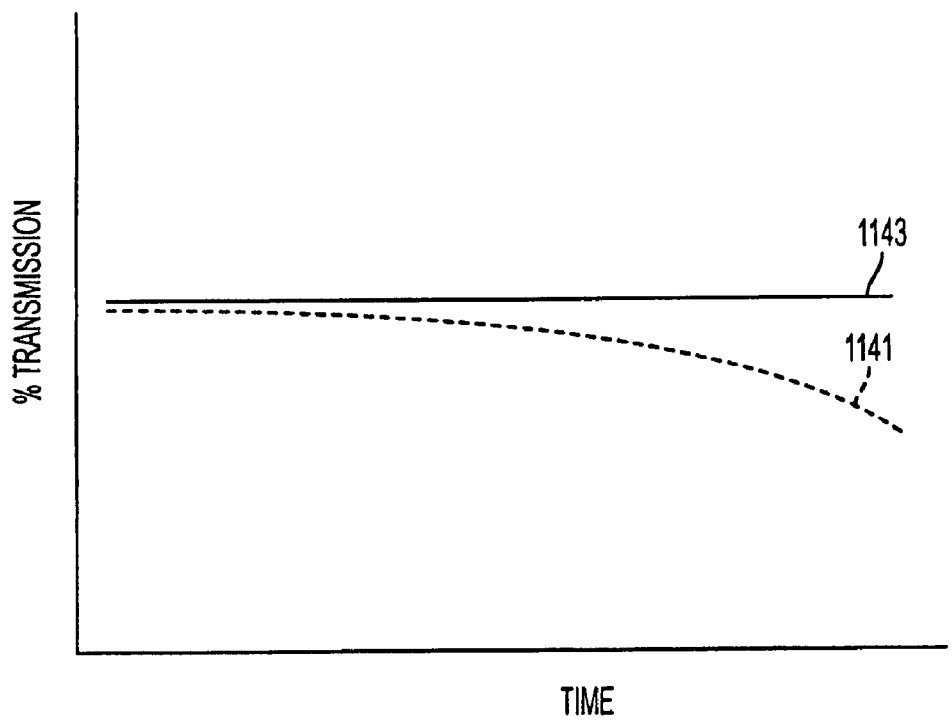
FIG. 12 provides a graph of how the spectroscope can be used for dynamic scaling.

FIG. 12 provides for adjustment of the sample channel by dynamic scaling or normalization over time. It is known that over time the operation of a spectroscope will change, casing the measured spectrum to change due to parts heating up or wearing out. This is particularly true of light sources. This is indicated by line (1141) showing how over time the transmission of a given wavelength has drifted. Effectively, this caused the spectroscope to loose its calibration. Because such changes can be detected by the reference channel (211) as not being due to the sample, the dynamic reference capability of the spectroscope (100) can be utilized to correct for the loss in calibration allowing the actual percent transmission to approach the ideal (1143) which is a constant.

FIGS. 9 through 12 have provided for a number of different benefits from the ability to dynamically reference by providing two optical paths (211) and (213). In particular, the spectroscope (100) can provide for wavelength dependent structuring of the spectrum which is used to interrogate the sample. This structuring may be spatial structuring where particular elements of the light are controlled based on their spatial positioning, or may be temporal structuring where the light is modulated over time.

In operation, any mirror arranged at the preselected +X° state will direct incident wavelengths toward the sample detector (203) while mirrors at the −X° state will direct incident wavelengths toward the reference detector (201) or vice-versa, depending on specific arrangement. Further, when the mirrors are between states, the light may be directed into a light trap (111) as shown in FIG. 1.

It should be apparent that with a generally single wavelength, or small wavelength band, incident on each of the mirrors in the MMA (107), one can adjust the mirrors to supply those wavelength bands incident on the mirrors, to either detector (201) and (203) individually or in any combination. The mid point (or 0°) state on most current MMA (107) devices is generally unstable and therefore light cannot be accurately directed elsewhere than at the two states. However, it can be recognized that if a third position of the mirror is sufficiently stable, this position can be used to provide for a third channel. In a preferred embodiment, this third channel would be for a dark signal measurement where there is no light incident on either the reference channel (211) or sample channel (213). As indicated in FIG. 1, with the mirrors arranged at a third state (such as 0°) the wavelengths are directed into an optical trap (111), rendering both detectors (201) and (203) temporarily dark. This allows each detector (201) and (203) to take a "dark signal" measurement simultaneously saving processing steps. Additionally, even without the third position, all wavelengths can be directed to either detector (201) or (203) thereby removing all incident radiation from the other detector (201) or (203), which also enables near real-time dark signal measurement at the currently dark detector (201) or (203). This operation provides for additional calibration in determining "dark noise" (effectively the amount of light incident on the detectors (201) and (203) which is not being purposefully directed to them by action of the MMA (107) in addition to the thermal response of detectors (201) and (203)), which can then be nulled by the spectroscope (100) control system.

Figures 13A, 13B:
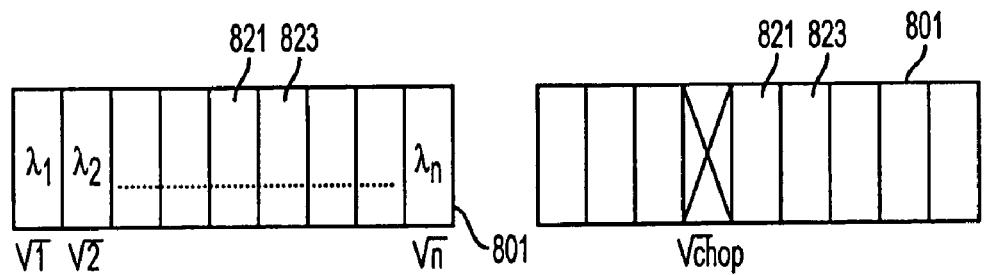
FIG. 13 provides for two indications of how wavelength segments of the spectrum can be modulated to provide for Fast Fourier Transform (FFT) analysis (FIG. 13A) and optical chopping (FIG. 13B).

It will also be understood that while FIG. 2 shows the monitoring of a single band in a scanning mode. FIG. 13 provides for a couple of examples of how spectrum columns (821) can be modified to perform some types of structuring. In FIG. 13A, each column has its bandwidth frequency modulated at independent frequencies so as to provide for Fast Fourier Transform (FFT) analysis. In an alternative approach shown in FIG. 13B instead of modulating each wavelength at a different frequency, each band can be modulated at the same frequency sequentially to provide signal-to-noise improvement via optical chopping. The spectroscope (100) can also be used to measure multiple bands simultaneously using the MMA (107) to temporally process the incident radiation simply by altering the frequency that each individual wavelength band is modulated. This in turn imparts a temporal structure to the incident radiation. This methodology enables the spectroscope (100) to read all wavelengths simultaneously, or multiplexed, as apposed to individually scanning each individual wavelength or wavelength band at either detector (201) or (203). This is simply an alternative method for spectral processing utilizing the same spectroscope (100). While the embodiment shown in FIG. 1 uses the MMA (107) for spectral filtering, an alternative embodiment may use the MMA (107) for spatial, spectral, or temporal filtering, thus enabling an alternative means of data processing, such as Hadamard Transform Spectroscopy or Fourier Transform Spectroscopy respectively.

The use of an MMA for Hadamard Transform Spectroscopy and Fourier Transform spectroscopy has been documented by DeVerse et. al. in "Realization of the Hadamard Multiplex Advantage Using a Programmable Optical Mask in a Dispersive Flat-Field Near-Infrared Spectrometer." *Applied Spectroscopy*, vol. 54 No. 12, pgs. 1751-1758 (2000), the entire disclosure of which is herein incorporated by reference. However, in DeVerse, implementations were limited due to the fact that only a single optical channel was utilized. Operating the spectroscope (100) as a Hadamard or Fourier Transform spectral analyzer and utilizing the dual channel nature of spectroscope (100), and algorithms known to those versed in the art of signal processing to deconvolute the reference and sample channels spectral content, spectroscope (100) is able to dynamically calibrate itself and/or scale output using implementations similar to those of DeVerse.

Further, it should be recognized that the spectroscope (100) is generally not limited by hardware configuration to any particular analysis technique but may be used for a variety of spectroscopy techniques including, but not limited to, those described in Spudich et al. "Potential for Using a Digital Micromirror Device as a Signal Multiplexer in Visible Spectroscopy." *Applied Spectroscopy*, vol. 57 No. 7, pgs. 733-736 (2003); U.S. Pat. No. 6,781,691; and United States Patent Publications US 2004/0239923 and US 2004/0169858. The entire disclosure of all of these documents is herein incorporated by reference.

Generally, as should be apparent from the FIGS., the spectroscope (100), utilizing the MMA (107), allows for the control system to select any wavelength band or bands for sampling, and to temporally structure bands, without requiring hardware reconfiguration. Instead, the component wavelength band(s) desired is simply selected by the control system based on what is available in the incident light, and how it instructs MMA (107). After that, the selected band(s) being used for sampling can be referenced against a reference signal with relative ease simply by redirecting the band(s) to the reference path. The measurement of a sample therefore shows good accuracy and stability for a spectroscope (100) having a high number of useable and alterable spectrums without need of hardware reconfiguration.

The spectroscope (100) described herein can be useful for field measurements, laboratory measurements, and/or process measurements due to the fact that it is capable of real-time scaling and normalization of any illumination source through the use of multiple light channels. The spectroscope (100) is also generally small enough to be easily portable and is capable of stand-alone operation via an integrated dedicated spectral processor or other electronic or similar control system, whether integrated, remote, or interconnected by a recognized communication system that can both control the device and interpret its output. The device can be controlled remotely via a computer, a PLC, or another controller using any type of computer interface known now or later discovered including, but are not limited to, RS232, USB, Ethernet, WiFi, and Bluetooth.

In an embodiment of the spectroscope (100), the housing (101) of the spectroscope can be formed into a process hardened, field portable, broadband optical monitor of a generally reasonable size for easy portability and field use.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A spectroscope comprising:
   a Micro Mirror Array (MMA) comprising a plurality of mirrors; each of said mirrors being switchable between a first and a second position;
   a light source having a spectrum; and
   at least two detectors;
   wherein said light source is spatially dispersed across said MMA in such fashion that a first group of said mirrors, can direct a first portion of said spectrum along a first light path to a first of said at least two detectors by being placed in said first position;
   wherein a second position of said mirrors can direct a second portion of said spectrum along a second light path to a second of said at least two detectors by being placed in said second position; and
   wherein said first light path includes a sample to be analyzed.

2. The spectroscope of claim 1 wherein said light source is a broad band light source.

3. The spectroscope of claim 1 wherein said light source is a narrow band light source.

4. The spectroscope of claim 1 wherein said second light path does not include a sample to be analyzed.

5. The spectroscope of claim 4 wherein output from said second detector is used as a reference for output from said first detector.

6. The spectroscope of claim 1 wherein said MMA comprises a Digital Micromirror Device (DMD).

7. The spectroscope of claim 1 further comprising an input slit through which said light passes prior to reaching said MMA.

8. The spectroscope of claim 7 wherein columns of said spectrum correspond to a spectral dimension of dispersion and rows correspond to a spatial dimension of said input slit.

9. The spectroscope of claim 8 wherein said plurality of mirrors are arranged into a plurality of rows and columns.

10. The spectroscope of claim 9 wherein said columns of said spectrum are incident on said MMA so as to align with said columns of mirrors.

11. The spectroscope of claim 9 wherein said columns of said spectrum are incident on said MMA so as to align with a diagonal of said rows and said columns of said mirrors.

12. The spectroscope of claim 1 wherein said MMA performs spectral separation of said spectrum.

13. The spectroscope of claim 1 wherein said MMA can reversibly direct said first portion along said first and said second path and said second portion along said first and said second path in such fashion that when one of said portions is directed to said first path, the other of said portions is directed to said second path and vice-versa.

14. A method of performing spectroscopy, the method comprising:
   providing a spectroscope including:
      a Micro Mirror Array (MMA) comprising a plurality of mirrors; each of said mirrors being switchable between a first and a second position; and
      at least two detectors;
   separating light into a spectrum;
   directing said spectrum to said MMA such that a first portion of said spectrum is incident on a first group of said mirrors and a second portion of said spectrum is incident on a second group of said mirrors;

instructing said MMA to arrange said first and said second group of mirrors such that:

said first portion is directed down a first light path including a sample to be analyzed to a first of said detectors; and said second portion is directed down a second light path which does not include said sample to be analyzed to a second of said detectors;

instructing said MMA to arrange said first and said second group of mirrors such that:

said second portion is directed down said first light path to a first of said detectors; and said first portion is directed down said second light path to a second of said detectors;

comparing an output from said first and said second detector to provide an indication of the composition of said sample.

15. The method of claim 14 wherein in said step of comparing said spectrum has been temporally structured by said steps of instructing.

16. The method of claim 15 wherein said temporal structuring is dependent on wavelength in said spectrum.

17. The method of claim 16 wherein said temporal structuring enables simultaneous processing of each of said wavelengths.

18. The method of claim 14 wherein in said step of comparing said spectrum has been spatially structured by said steps of instructing.

19. The method of claim 18 wherein said spatial structuring is dependent of wavelength in said spectrum.

20. The method of claim 14 wherein in said step of comparing said spectrum has been temporally encoded so as to optically chop the spectrum to improve a signal-to-noise ratio by said steps of instructing.

21. The method of claim 14 wherein in said step of comparing said spectrum has been dynamically scaled by said steps of instructing.

22. The method of claim 14 wherein in said step of comparing said spectrum has been dynamically filtered by said steps of instructing.

23. The method of claim 14 wherein in said step of comparing said spectrum has had the resolution dynamically altered by said steps of instructing.

24. The method of claim 14 wherein in said step of comparing a signal-to-noise ratio has been dynamically increased by said steps of instructing.

25. The method of claim 14 wherein said second light path does not include any samples prior to said second detector.

26. The method of claim 14 wherein said second light path includes a gas correlation cell.

* * * * *